US012566152B2

(12) United States Patent
Hellein

(10) Patent No.: US 12,566,152 B2
(45) Date of Patent: Mar. 3, 2026

(54) MOBILE SYSTEM FOR CALIBRATING, VERIFYING AND/OR ADJUSTING A SENSOR AND METHOD FOR CALIBRATING, VERIFYING AND/OR ADJUSTING A SENSOR

(71) Applicant: Endress+Hauser Group Services AG, Reinach (CH)

(72) Inventor: Bernhard Hellein, Pixendorf (AT)

(73) Assignee: Endress+Hauser Group Services AG, Reinach (CH)

( * ) Notice: Subject to any disclaimer, the term of this patent is extended or adjusted under 35 U.S.C. 154(b) by 979 days.

(21) Appl. No.: 17/632,144

(22) PCT Filed: Jul. 27, 2020

(86) PCT No.: PCT/EP2020/071073
§ 371 (c)(1),
(2) Date: Feb. 1, 2022

(87) PCT Pub. No.: WO2021/023537
PCT Pub. Date: Feb. 11, 2021

(65) Prior Publication Data
US 2022/0349854 A1     Nov. 3, 2022

(30) Foreign Application Priority Data
Aug. 2, 2019    (DE) .......................... 102019120897.1

(51) Int. Cl.
*G01N 27/416*     (2006.01)
*C02F 1/26*     (2023.01)
*G01N 33/00*     (2006.01)

(52) U.S. Cl.
CPC ......... *G01N 27/4163* (2013.01); *C02F 1/265* (2013.01); *G01N 33/007* (2013.01)

(58) Field of Classification Search
CPC ........... G01N 27/4163; G01N 27/3274; G01N 27/4175; G01N 33/0006; G01N 33/007; C02F 1/265
See application file for complete search history.

(56) References Cited

U.S. PATENT DOCUMENTS 5,403,497 A      4/1995   Schultz
6,627,461 B2 *   9/2003   Chapman et al.
7,312,085 B2 *  12/2007   Chou et al.
(Continued)

FOREIGN PATENT DOCUMENTS

CN      102471796 A     5/2012
CN      109959698 A     7/2019
(Continued)

*Primary Examiner* — Jill A Warden
*Assistant Examiner* — Velvet Elizabeth Heron
(74) *Attorney, Agent, or Firm* — Christopher R. Powers; Endress+Hauser (USA) Holding, Inc.

(57) ABSTRACT

The present disclosure includes a mobile system for calibrating, verifying and/or adjusting a sensor, the mobile system having a valve unit, wherein by setting, in particular controlling, the valve unit, the process variable present at a calibration site can be set, in particular controlled, to at least one specifiable reference value for the process variable. The present disclosure further includes a method for calibrating, verifying and/or adjusting a sensor by means of the mobile system.

12 Claims, 2 Drawing Sheets

(56) References Cited

U.S. PATENT DOCUMENTS

| | | | |
|---|---|---|---|
| 8,221,682 | B2 * | 7/2012 | Ammann et al. |
| 9,890,882 | B2 * | 2/2018 | Zeko et al. |
| 2007/0168145 | A1 | 7/2007 | Beyer et al. |
| 2009/0018426 | A1 | 1/2009 | Markle et al. |
| 2009/0057145 | A1 | 3/2009 | Vincent |
| 2010/0094114 | A1 | 4/2010 | Robinson et al. |
| 2015/0168436 | A1 | 6/2015 | Kathe et al. |
| 2015/0185174 | A1 | 7/2015 | Aleisa et al. |
| 2015/0330928 | A1 | 11/2015 | Korslund |
| 2016/0095475 | A1 | 4/2016 | Brennan et al. |
| 2017/0138853 | A1 | 5/2017 | Konishi et al. |
| 2018/0231496 | A1 * | 8/2018 | Brennan ............ G01N 27/4163 |
| 2019/0060834 | A1 * | 2/2019 | Katz ..................... B01D 61/10 |

FOREIGN PATENT DOCUMENTS

| | | | |
|---|---|---|---|
| DE | 102011086392 | A1 | 5/2013 |
| DE | 112013005089 | T5 | 7/2015 |
| DE | 102016121439 | A1 | 5/2018 |
| EP | 1238623 | A2 | 9/2002 |
| JP | 0526853 | A | 2/1993 |
| JP | 09288054 | A | 11/1997 |
| JP | H09288054 | A | 11/1997 |
| KR | 100428751 | B1 | 4/2004 |
| KR | 101612373 | B1 | 4/2016 |
| UA | 16786 | U * | 8/2006 |
| WO | 03017831 | A1 | 3/2003 |

* cited by examiner

MOBILE SYSTEM FOR CALIBRATING, VERIFYING AND/OR ADJUSTING A SENSOR AND METHOD FOR CALIBRATING, VERIFYING AND/OR ADJUSTING A SENSOR

CROSS-REFERENCE TO RELATED APPLICATIONS

The present application is related to and claims the priority benefit of German Patent Application No. 10 2019 120 897.1, filed Aug. 2, 2019, and International Patent Application No. PCT/EP2020/071073, filed Jul. 27, 2020, the entire contents of which are incorporated herein by reference.

TECHNICAL FIELD

The invention relates to a mobile system for calibrating, verifying and/or adjusting a sensor for determining the process variable of a process medium. Furthermore, the invention relates to a method for calibrating, verifying and/or adjusting a sensor.

BACKGROUND

The process variable which can be determined with the sensor is, especially, an analysis measurement variable, which is determined by the concentration of one or more substances in the measurement medium (so-called analyte or analytes), for example a concentration or an activity or a sum of concentrations of a plurality of analytes. Sensors of this type are used in the analysis of measurement mediums in laboratory and process measurement technology in many fields of chemistry, biochemistry, pharmacy, biotechnology, food technology, water management and environmental metrology. The sensor for determining the process variable or the analysis measurement variable is, for example, a potentiometric (e.g., ion selective electrode (ISE), for example the known pH glass electrode) or amperometric sensor (for example amperometric disinfection sensor). Further examples of sensors are those based on electrolyte-insulator-semiconductor layer stacks (abbreviated as: EIS), e.g. ISFET sensors, inductively or capacitively operating conductivity sensors or (spectrometry) photometrically operating sensors, such as turbidity sensors. Applicant sells a large number of such sensors for determining an analysis measurement variable in a wide variety of embodiments.

Such sensors usually have to be calibrated, verified and/or adjusted. In this case, for example, a reference sensor serving as a reference or a measured value determined therewith that is assumed to be correct is used as a reference value. Calibration usually refers to the detection of a discrepancy between the measured value measured with the sensor and the reference value assumed to be correct. The verification also comprises determining the deviation and its evaluation. Adjustment is understood to mean adapting the sensor in such a way that its measured value matches the reference value. The calibrating, verifying and/or adjusting generally takes place at least during the commissioning of the sensor or in some cases also repeatedly—for example at regular calibration intervals—if, for example, an aging-related drift of the sensor is to be assumed.

In practice, a plurality of different reference values are often used in the calibration, verification and/or adjustment of a sensor (also: multipoint calibration). For this purpose, a plurality of calibration standards that have different values, especially predetermined values, is used for the process variable that is determinable with the sensor (or the reference sensor), especially an analysis measurement variable. The sensor to be calibrated, verified and/or adjusted and the reference sensor are then successively brought into contact with the calibration standards, for example. For example, the calibration standards are present as a series of calibration liquids (e.g., calibration solutions, some buffer solutions), into which the sensor to be calibrated, verified and/or adjusted and in some cases also the reference sensor are introduced in succession.

In some cases, the reference sensor is in practice used only in the manufacture of the calibration liquid and not during calibration, verification and/or adjustment of the sensor. The measured value for the process variable detected with the reference sensor during the production of the calibration liquid is assigned to the calibration liquid. Due to a temperature dependence that is often present, the temperature is additionally measured in this case during subsequent calibration, verification and/or adjustment. In the event that the temperature during the production of the calibration liquid differs from the temperature during the calibration, verification and/or adjustment of the sensor, this temperature dependence is corrected by calculation.

This proves to be relatively complicated, not least because the sensor or sensors in this case have to be subjected to a thorough cleaning in each case, in order to effectively prevent a mutual contamination of the calibration liquids with respect to one another by any residues on the sensor(s).

SUMMARY

The invention is therefore based on the object of simplifying the calibration, verification and/or adjustment of a sensor.

The object is achieved by a mobile system for calibrating, verifying and/or adjusting a sensor and by a method for calibrating, verifying and/or adjusting a sensor for determining a process variable of a process medium dependent on a salt concentration, with which method a mobile system is used.

With regard to the mobile system, the object is achieved by a mobile system for calibrating, verifying and/or adjusting a sensor for determining a process variable of a process medium, which is dependent on a salt concentration and comprises a conveying circuit that is designed to convey a calibration liquid introduced therein, the system having:
- a fluid line;
- a bypass fluid line, which is connected to the fluid line via a first connection point and a second connection point in a bypass to a first section of the fluid line, having a filter unit, which is configured for continuous desalinization of a portion of the calibration liquid conveyed through the bypass fluid line;
- a pump arranged in the fluid line, which is designed to convey the calibration liquid in a conveying direction through the conveying circuit;
- a calibration site arranged in a second section of the fluid line that is different from the first section, to which the sensor to be calibrated, verified and/or adjusted and a reference sensor serving for the measurement of the process variable can be introduced into the conveying circuit and/or connections arranged in a second section of the fluid line that is different from the first section, by means of which connections at least one interchangeable fitting serving as a calibration site can be integrated into the conveying circuit, wherein the sensor to be calibrated, verified and/or adjusted and a reference sensor that serves for measuring the process variable can be introduced into the conveying circuit with the at least one interchangeable fitting, and an adjustable valve unit, by means of which a ratio of the portion of the calibration liquid conveyed through the bypass fluid line to a portion of the calibration liquid conveyed through the first section of the fluid line can be set, wherein, by setting, especially controlling, the valve unit, the process variable present at the calibration site can be set, especially controlled, to at least one specifiable reference value for the process variable.

According to the invention, the process variable of the calibration liquid can be adjusted to the at least one specifiable reference value by setting the valve unit. The setting of the valve unit determines the portion of the calibration liquid flowing through the bypass line and the first section of the fluid line. In this way, the proportion that is continuously desalinated in the filter unit of the bypass line and thus the salt content of the calibration liquid ultimately present at the calibration site is set. Given that the process variable depends on a salt concentration of the calibration liquid, the reference value is also adjustable thereby.

The filter unit is especially a desalination plant, for example a so-called mixed bed filter. The bypass of the conveying circuit is formed here by the second section of the fluid line branching into the first section and the bypass fluid line at the first connection point. This bypass fluid line and the first section open again at the second connection point into the second section, thereby closing the conveying circuit.

The advantages of the invention are as follows:

The mobile system enables the subsequent setting of the process variable to the at least specifiable reference value. "Subsequent" means that the calibration liquid remains in the conveying circuit. The sensor and the reference sensor also remain directly in contact with the calibration liquid when the process variable is being set to the at least one reference value. As a result, no prior cleaning of the sensors is necessary any longer. Advantageously, a plurality of different reference values can also be set in succession;

Especially, reference values of the calibration liquid that are highly sensitive to the salt content of the calibration liquid at the calibration site are also adjustable by the solution according to the invention. By contrast, calibrating, verifying and/or adjusting, for example, a conductivity sensor having a measuring range less than 50 μS/cm with the calibration solutions known from the prior art is difficult, or not at all possible, to implement, due to its high sensitivity to contamination;

With the mobile system, a higher accuracy can be achieved, compared to calibration, verification and/or adjustment, with which the reference sensor is only used in the production of calibration liquids and a temperature dependence of the process variable must be computationally corrected by means of a temperature measurement. In the latter case, a continuous inaccuracy of the temperature measurement is present, whereas, with the mobile system according to the invention, only the inaccuracy of the measurement with the reference sensor is present;

It is a mobile system. Especially, the system is preferably compact as a portable mobile system, for example with a total weight less than 10 kg. This advantageously enables an on-site calibration of a sensor at its intended place of use.

In one embodiment of the mobile system, this comprises a container that is arranged in the second section of the fluid line and is connected to the fluid line by an inlet for the inflow of the liquid from the second section of the fluid line into the container and by an outlet for the outflow of the liquid from the container into the second section of the fluid line.

By means of the container, the calibration liquid can be added into the mobile system and a volume of calibration liquid required for calibrating, verifying and/or adjusting the sensor can be provided as simply as possible. For this purpose, the container typically comprises a volume smaller than 10 l, for example 0.5 to 5 l.

In one embodiment of the mobile system, the container forms the calibration site, so that during the calibration, verification and/or adjustment of the sensor, the sensor to be calibrated, verified and/or adjusted and the reference sensor dip into the calibration liquid contained in the container.

In a further embodiment of the mobile system, this is an open container, wherein a gas that is contained in the ambient air surrounding the open container forms salts in the calibration liquid by means of a chemical reaction between the gas and the calibration liquid contained in the open container. Thus, starting from an initial salt concentration, the salt concentration of the calibration liquid is increased at the calibration site. In combination with the continuous desalination according to the invention through the filter unit in the bypass line, both an increase and/or a decrease in the salt concentration at the calibration site is thereby made possible.

Of course, within the scope of the invention, a closed container or a conveying circuit without a container is also possible, wherein in this case only the reduction of the salt concentration at the calibration site is possible.

In an especially preferred development of the mobile system, an adjustable controller of the valve unit controls the valve unit such that the process variable present at the calibration site has successive different specifiable reference values for the process variable, especially at least two different specifiable reference values for the process variable, while the calibration liquid, the sensor to be calibrated, verified and/or adjusted and the reference sensor serving as a reference remain in the conveying circuit.

With the mobile system, especially the successive activation of the different reference values is possible without the need for complex cleaning of the sensor and, where applicable, of the reference sensor in the case of handling with the calibration solutions known from the prior art. The sensor and reference sensor remain constantly in contact with the calibration liquid according to the invention. This has the different reference values in succession only due to adjustment of the valve unit. A multi-point calibration is thus especially simple.

In an especially preferred embodiment of the mobile system, the mobile system is a mobile system for calibrating, verifying and/or adjusting a conductivity sensor, which has especially a measuring range that is limited by a maximum conductance of less than 50 μS/cm, preferably less than 10 μS/cm. As mentioned above, in such a measuring range a calibration, verification and/or adjustment of a conductivity sensor with calibration solutions is highly demanding. This applies especially in the case of an on-site calibration with which no laboratory conditions can be achieved. For example, the setting of a reference value less than 1 μS/cm with calibration solutions is virtually excluded in this case.

In one embodiment of the mobile system, the pump is arranged in the second section of the fluid line. As a result, the pump enables reliable conveyance through the entire conveying circuit, e.g., the second section of the fluid line, and the bypass line connected in the bypass between the first and the second connection point and the first section of the fluid line.

In one embodiment of the mobile system, the pump is arranged adjacent to the first connection point, in relation to the conveying direction of the pump substantially upstream of the first connection point.

In a further embodiment of the mobile system, the valve unit is arranged at the second connection point.

The valve unit is, for example, an adjustable 2-by-3-way valve or a unit made up of a plurality of mutually interacting valves. The valve unit according to the invention is preferably arranged at the second connection point. As a result, the same pressure is present in the bypass line and in the first section of the fluid line. Of course, it is also possible within the scope of the invention to arrange the valve unit at the first connection point and/or to provide a further valve unit on the latter.

In a further embodiment of the mobile system, at least partially desalinated, especially fully desalinated water is introduced as calibration liquid into the feed circuit.

In a further embodiment of the mobile system, the controller of the valve unit and/or the valve unit itself can be manually actuated. The calibration, verification and/or adjustment of the sensor is thus performed, for example, by an application technician manually adjusting or controlling the controller or the valve unit, until a process variable determined with the reference sensor matches with the specifiable reference value used in the calibration, verification and/or adjustment. In the case of a multi-point calibration, this is repeated as necessary in successive steps.

In a further embodiment of the mobile system, it comprises a control/evaluation unit that comprises the controller, wherein the control/evaluation unit is connected to the valve unit and can be connected to the reference sensor. The control/evaluation unit enables a (semi-)automatic control of the control/evaluation unit, because it is designed to control the valve unit. The mobile system can, of course, be designed both for manual and for (semi-)automatic control.

In a preferred embodiment of the mobile system, the components thereof, especially the fluid line, the bypass fluid line, the filter unit, the container, the pump and the valve unit, are formed as components that can be snapped onto one another. The snap-together mobile system enables an especially simple, substantially tool-free (i.e., without the use of additional tools) design of the mobile system and/or replacement of its components. For example, the replacement of the filter unit, which gradually gets more clogged during operation, is very easy.

In a further embodiment of the mobile system, the fluid line and/or the bypass line have a thermoplastic material, especially polytetrafluoroethylene (PTFE). They can, for example, consist of this material, or be at least partially lined therewith.

With regard to the method, the object is achieved by a method for calibrating, verifying and/or adjusting a sensor for determining a process variable of a process medium depending on a salt concentration, wherein a mobile system is used, comprising a conveying circuit that is designed to convey a calibration liquid introduced therein, comprising:
  a fluid line;
  a bypass fluid line, which is connected to the fluid line via a first connection point and a second connection point in a bypass to a first section of the fluid line, having a filter unit, which is configured for continuous desalinization of a portion of the calibration liquid conveyed through the bypass fluid line;
  a pump arranged in the fluid line, which is designed to convey the calibration liquid in a conveying direction through the conveying circuit;
  an adjustable valve unit, by means of which a ratio of the portion of the calibration liquid conveyed through the bypass fluid line to a portion of the calibration liquid conveyed through the first section of the fluid line can be set,
wherein the method includes the steps of:
  introducing the sensor to be calibrated, verified and/or adjusted and a reference sensor serving for the measurement of the process variable into the conveying circuit at a calibration site arranged in the second section of the fluid line and/or into at least one interchangeable fitting, which serves as a calibration site and is integrated into the conveying circuit of the mobile system by connections arranged in the second section the fluid line;
  setting, especially controlling, the valve unit such that the process variable present at the calibration site has a specifiable reference value for the process variable.

In one embodiment of the method, the setting, especially controlling, of the valve unit is carried out with the aim that a measured value of the process variable determined with the reference sensor matches the specifiable reference value.

In a further development of the method, this comprises:
  recurrent setting, especially controlling, of the valve unit such that the process variable present at the calibration site has different specifiable reference values at successive instants for the process variable, especially at least two different specifiable reference values for the process variable, wherein the calibration liquid, the sensor to be calibrated, verified and/or adjusted, and the reference sensor serving as a reference at the successive instants during the recurrent setting, especially controlling, of the valve unit remain in the conveying circuit.

BRIEF DESCRIPTION OF THE DRAWINGS

The invention will be explained further with reference to the figures, which are not true-to-scale, wherein the same reference signs designate the same features. For reasons of clarity, or if it appears sensible for other reasons, previously-noted reference signs will not be repeated in the following figures.

The following are shown.

DETAILED DESCRIPTION

Figures 1A, 1B:
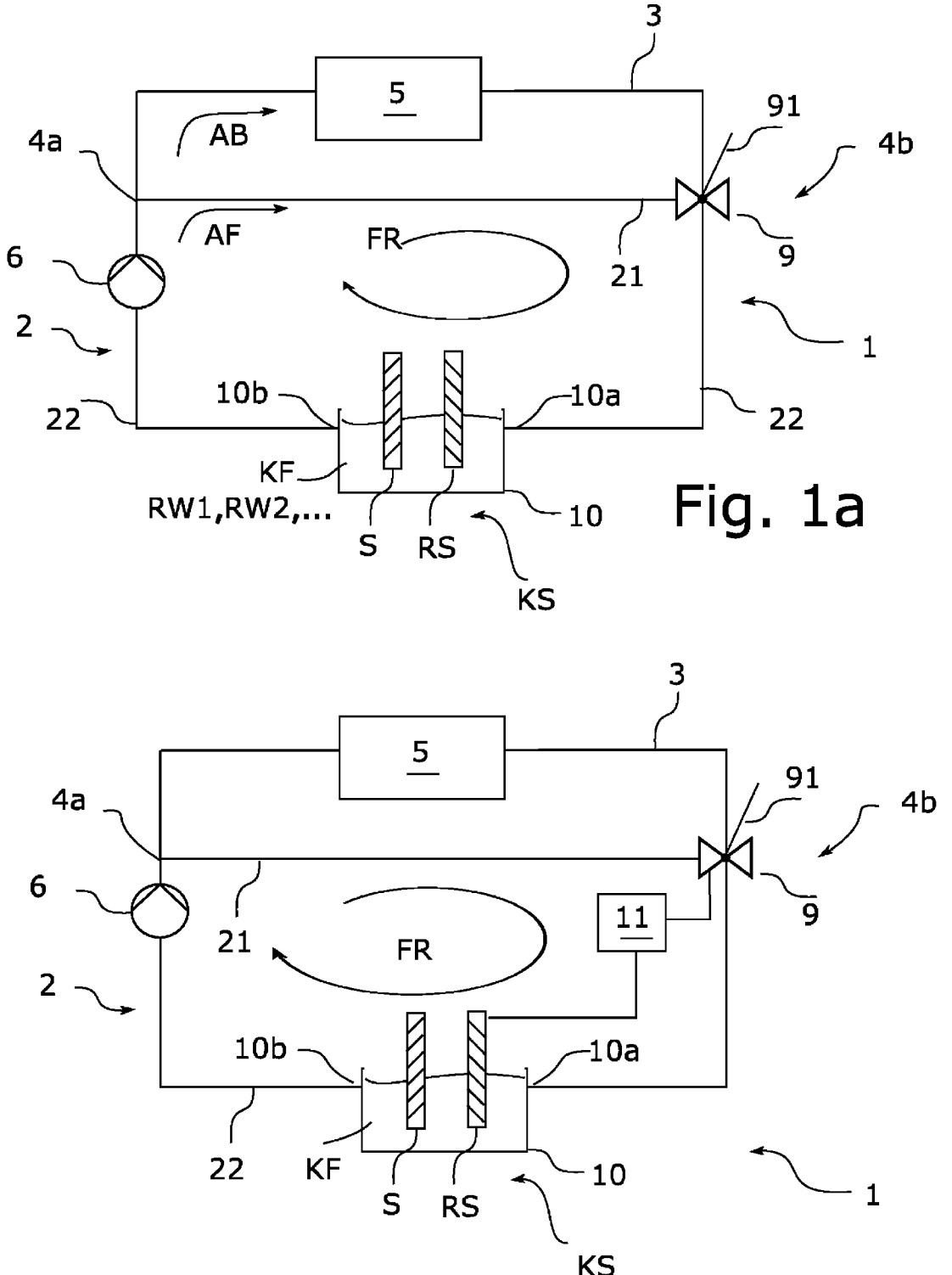
FIG. 1a shows a first embodiment of the mobile system.
FIG. 1b shows a further embodiment of the mobile system.

FIG. 1a shows a first embodiment of the mobile system for calibrating, verifying and/or adjusting a sensor S. The system comprises a conveying circuit 1 having a fluid line 2. In this embodiment, the conveying circuit 1 is formed by a jointly guided second section 22 and a first section 21 of the fluid line 2 and a bypass line 3 guided in a bypass for this purpose. At a first connection point 4a, the second section 22 branches into the first section 21 and the bypass line 3. A calibration liquid KF is conveyed through the conveying circuit 1 in a conveying direction FR (in this case in the clockwise direction) by means of a pump 6, namely through the first 21 and second section 22 and through the bypass line. The pump 6 is arranged in the second section 22. It is designed to convey a conveying quantity of 100-1000 l/h, for example approximately 300 l/h, such as for example in the case of a commercially available aquarium pump.

At a second connection point 4b, the first section 21 and the bypass line 3 open again into the second section 22, so that the conveying circuit 1 is thus closed. A first portion AB of the calibration liquid is conveyed through the bypass line 3 and a second portion AF is conveyed through the first section 21. Only the portion AB conveyed through the bypass line 3 is continuously desalinated by means of a filter unit 5 arranged therein. This is designed as a mixed-bed filter that comprises a cation-exchange and anion-exchange resin. The filter unit 5 is very easy to replace, because it is a snap-together system. Empirical values of Applicant show that, with typical applications, the filter unit 5 can be used for the calibration, verification and/or adjustment of a sensor S up to approximately 40 times before a replacement is required.

The portion AB of the calibration liquid KF that is conveyed through the bypass line 3 and thus continuously desalinated is determined by setting an adjustable valve unit 9 with a controller 91. The controller 91 can be manually actuated or adjusted in the embodiment shown in FIG. 1a. Preferably, the valve unit 9 according to the invention is arranged at the second connection point 4b, i.e., at the downstream branching of the bypass, as a result of which the same pressure is present in the bypass line 3 and in the first section 21. Alternatively, however, it is quite possible within the scope of the invention to arrange the valve unit 9 at the first connection point 4a, i.e., at the upstream branching of the bypass. Where appropriate, it is also possible for the mobile system to have a plurality of mutually interacting valve units, e.g., the valve unit 9 according to the invention and a further valve unit 12 (shown in FIG. 2).

In this embodiment, the mobile system according to the invention further comprises a calibration site KS, at which the sensor S to be verified and/or adjusted and a reference sensor RS serving for the measurement of the process variable can be introduced into the conveying circuit 1.

In this embodiment, the calibration site KS is formed by an open container 10 into which the calibration liquid KF can be filled and into which the sensor S and the reference sensor RS are jointly immersed during the calibration, verification and/or adjustment of the sensor S and are thereby introduced into the conveying circuit 1. These are connected to a (in some cases common) transmitter unit (not shown), which serves for processing and/or forwarding a measurement signal that is respectively generated by the sensor S and the reference sensor RS and is dependent on the process variable. The measured value indicated by the reference sensor RS is assumed to be correct. For this purpose, reference sensor RS is calibrated in practice at regular intervals, for example annually.

The container 10 comprises a volume of approximately 1.5 liters. As a calibration liquid KF, fully or partially desalinated water is used as the starting liquid, for example. The container 10 is integrated into the conveying circuit 1 by means of an inlet 10a arranged upstream in relation to the conveying direction FR and an outlet 10b arranged downstream thereof.

In the case of an open container 10, a gas that is contained in the ambient air surrounding the open container 10 forms salts by means of a chemical reaction between the gas and the calibration liquid KF contained in the open container 10. For example, partially or fully desalinated water reacts as calibration liquid KF with the ambient air by virtue of the fact that $CO_2$ accumulates and dissolves in the calibration liquid KF. As a result, the salt content and thus also, for example, the conductance as a process variable increases steadily. Due to the fact that the portion AB of the calibration liquid KS simultaneously flowing through the bypass line 3 is continuously desalinated in the conveying circuit f1, this effect can be compensated. As a result, the salt content at the calibration site KS and thus the process variable dependent on the salt content can be set to a stable reference value RW1. With the mobile system, a very small conductance of 0.5 μS/cm (Micro-Siemens per cm) can be set as a reference value for the process variable, for example.

During a conveyance through the conveying circuit 1, the setting of the valve unit 9 determines the salt content of the calibration liquid KF at the calibration site KS. Therefore, the process variable present at the calibration site KS can be set to the at least one reference value RW1; RW2, . . . by setting the valve unit 9.

In the case of a multi-point calibration, the valve unit 9 is preferably first set in such a way (for example manually) that the process variable at the calibration site KS assumes a first reference value RW1, wherein the sensor S is calibrated to this first reference value RW1. Subsequently, the process variable at the calibration site KS is set to a second reference value RW2 only by a changeover of the valve unit 9, and the sensor S is calibrated to this second reference value RW2 (or subsequently to further reference values RW3, RW4, . . . etc.). For this purpose, no changing of the calibration liquid KF in the mobile system is necessary, because substantially only the valve unit 9 is changed over. The sensor S and the reference sensor can remain unchanged in the mobile system.

In the embodiments shown in the exemplary embodiments, the container 10 is embodied as open. Of course, the container 10 according to the invention can alternatively also be designed as a closed or at least closable container 10. In this case starting from an initial salt content or an associated process variable, by setting the valve unit 9 at least the salt content at the calibration site KS can be reduced or the associated reference values RW1, RW2, . . . for the process variable can be set. If necessary, a salt can also be added to the container 10 once in an open or closable container 10.

FIG. 1b shows the mobile system according to the invention that is substantially already shown in FIG. 1a, wherein in addition a control/evaluation unit 11 connected to the valve unit 9, for example with a microprocessor, is additionally provided. The control/evaluation unit 11 can be connected to the reference sensor RS. By means of the control/evaluation unit 11, a largely automated calibration, verification and/or adjustment of the sensor S is possible.

Figure 2:
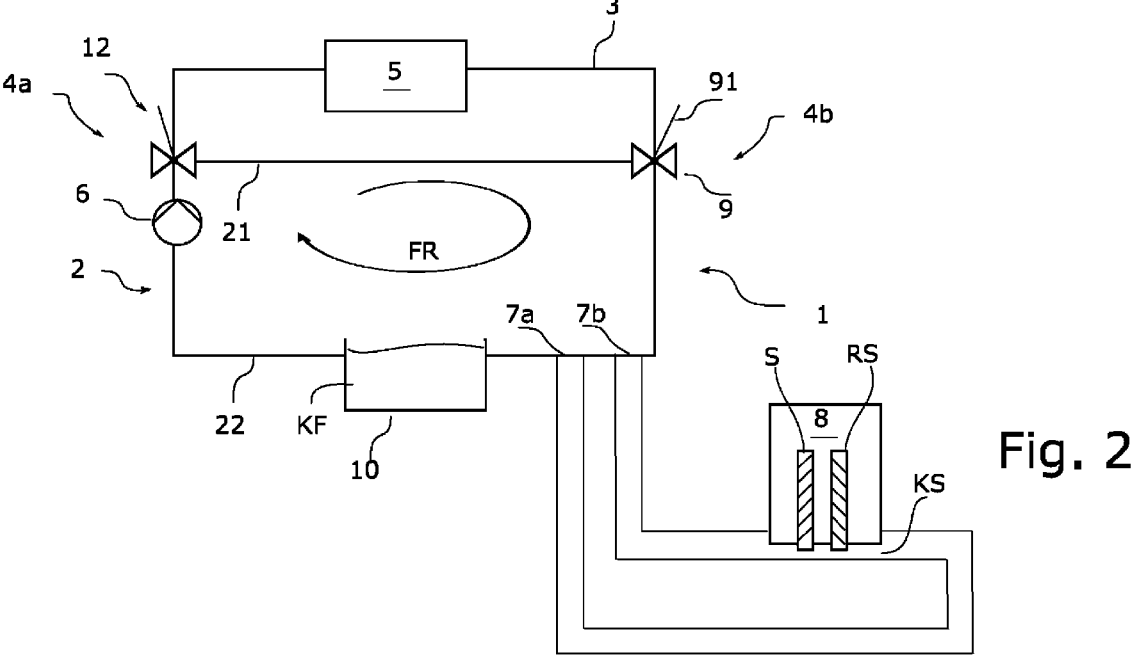
FIG. 2 shows a further embodiment of the mobile system.

FIG. 2 shows a further embodiment according to the invention. This also comprises the possibly open container 10 with the calibration liquid KF, which here only serves as a reservoir for the calibration liquid KF and not for introducing the sensor S and the reference sensor RS. In the embodiment shown in FIG. 2, two connections 7a, 7b are arranged in the second section 22. Via these connections 7a, 7b, an interchangeable fitting 8 serving as a calibration site KS can be integrated into the conveying circuit.

In the aforementioned industries, interchangeable fittings are widely used, with which sensors can be introduced into a process medium and removed without interrupting ongoing processes. The sensors are moved, manually or automatically, in an axial direction between a process position and a service position of the interchangeable fitting. The interchangeable fitting 8 shown in FIG. 2 is configured to receive two sensors, namely the sensor S to be calibrated, verified and/or adjusted and the reference sensor RS, and to introduce them into the conveying circuit 1. Alternatively, the calibration site KS can also have two interchangeable fittings 8 arranged in a pipeline, which are designed to introduce both the sensor S to be calibrated, verified and/or adjusted and the reference sensor RS into the conveying circuit 1. As an alternative to the embodiment shown in FIG. 2, the connections 7a,7b for integrating the interchangeable fitting 8 can also be arranged at other points of the second section 22, for example between the pump 6 and the first connection point 4a.

Of course, a combination of the embodiments shown in FIGS. 2 and 1a, 1b is also possible within the scope of the invention. For example, one of the two sensors S, RS (i.e., the sensor S to be calibrated, verified and/or adjusted and the reference sensor RS) can be arranged in a (open or closed or closable) container 10, and the other of the two sensors S, RS in the interchangeable fitting. In this case, the calibration site KS is formed both by the container 10 and by the interchangeable fitting 8. For example, the sensor S to be calibrated, verified and/or adjusted can be introduced into the conveying circuit 1 by means of the interchangeable fitting 8, and the reference sensor by means of the container 10. The latter case is advantageous, for example, when the intended location of use of the sensor S during operation is in the interchangeable fitting 8. In this case, the sensor S can remain at its intended place of use for calibrating, verifying and/or adjusting.

The fluid lines of the snap-together mobile system are designed as PTFE plastic hoses having a diameter of less than 10 mm, and the entire mobile system can have a total weight less than 10 kg, for example only about 5 kg.

Investigations of Applicant show that the mobile system achieves an accuracy of +/−2% during the calibration, verification and/or adjustment of the sensor S. For the conductivity as the process variable, such high accuracy cannot be met with the calibration solutions known from the prior art for all measurement ranges used in practice. This is especially true for smaller measurement ranges having a maximum conductance less than 50 μS/cm, especially less than 10 μS/cm.

The invention claimed is:

1. A mobile system for calibrating, verifying and/or adjusting a conductivity sensor configured to determine a conductance of a process medium, the mobile system comprising:

a conveying circuit configured to convey a calibration liquid, the conveying circuit comprising:

a fluid line including a first section and a second section;

a bypass fluid line, which is connected to the fluid line via a first connection point and a second connection point, as to bypass the first section of the fluid line;

a filter unit disposed in the bypass fluid line and configured to perform a continuous desalination of a portion of the calibration liquid conveyed through the bypass fluid line;

a pump disposed in the fluid line and configured to pump the calibration liquid in a conveying direction through the fluid line and the bypass fluid line simultaneously, wherein the second section of the fluid line is downstream of the second connection point with respect to the conveying direction, and the first section is upstream thereof;

an adjustable valve, wherein the adjustable valve is operable to set a ratio of the portion of the calibration liquid conveyed through the bypass fluid line, which is desalinated by the filter unit, to a portion of the calibration liquid conveyed through the first section of the fluid line;

a calibration site enabling the conductivity sensor and a reference conductivity sensor to be introduced into the conveying circuit, wherein either the calibration site is located within the second section of the fluid line or the calibration site, including an interchangeable fitting, is introduced into the conveying circuit via connections disposed in the second section of the fluid line, wherein the adjustable valve includes an adjustable controller configured to control the adjustable valve such that the conductance of the calibration liquid at the calibration site has selectable specified reference values.

2. The mobile system of claim 1, wherein the calibration site being located within the second section is given by a container disposed in the second section of the fluid line and connected to the fluid line by an inlet for the inflow of the calibration liquid from the second section into the container and by an outlet for the outflow of the calibration liquid from the container into the second section, and wherein the container is an open container.

3. The mobile system of claim 2, wherein the fluid line, the bypass fluid line, the filter unit, the container, the pump and the adjustable valve are each configured to be snap-fit to each other.

4. The mobile system of claim 1, wherein the pump is disposed in the second section of the fluid line, wherein the pump is disposed adjacent and substantially upstream of the first connection point with respect to the conveying direction of the pump, and wherein the valve is disposed at the second connection point.

5. The mobile system of claim 1, wherein the adjustable controller of the adjustable valve and/or the adjustable valve itself are/is manually actuated.

6. The mobile system of claim 1, further comprising a control/evaluation unit, which includes the adjustable controller, and wherein the control/evaluation unit is connected to the adjustable valve and is configured to be connected to the reference conductivity sensor.

7. The mobile system of claim 1, wherein the fluid line and/or the bypass fluid line include a thermoplastic material.

8. The mobile system of claim 7, wherein the thermoplastic material is polytetrafluoroethylene (PTFE).

9. A method for calibrating, verifying and/or adjusting a conductivity sensor, the method comprising:

pumping a calibration liquid in a conveying direction simultaneously through a fluid line and a bypass fluid line, which bypasses a first section of the fluid line to a calibration site;

continuously desalinating the calibration liquid conveyed through the bypass fluid line;

setting a ratio of a portion of the calibration liquid conveyed through the bypass fluid line to a portion of the calibration liquid conveyed through the first section of the fluid line;

introducing the conductivity sensor and a reference conductivity sensor into the calibration site; and setting the ratio such that a conductance of the calibration liquid at the calibration site has at least one specified reference value.

10. The method of claim 9, wherein the calibration liquid selected forms salts when reacting chemically with a gas contained in ambient air coming into contact with the calibration liquid.

11. The method of claim 9, wherein at least partially desalinated water is used as the calibration liquid.

12. The method of claim 9, further comprising:

recurrently setting and/or controlling a valve such that the conductance of the calibration fluid at the calibration site at successive instants has selected specified reference values for the process variable, wherein the calibration liquid, the conductivity sensor and the reference conductivity sensor remain in the a conveying circuit during the recurrent setting and/or controlling of the valve.

\* \* \* \* \*